United States Patent [19]

Leroux

[11] Patent Number: 4,893,944
[45] Date of Patent: Jan. 16, 1990

[54] NON-DESTRUCTIVE METHOD OF TESTING A WELD OBTAINED BY PRESSURE WELDING TWO METAL PARTS

[75] Inventor: Jöel Leroux, Evreux, France

[73] Assignee: Serimer, Société a Responsibilité Limitée, Levallois Perret, France

[21] Appl. No.: 291,629

[22] Filed: Dec. 29, 1988

[30] Foreign Application Priority Data

Dec. 30, 1987 [FR] France ................ 87 18362

[51] Int. Cl.$^4$ ............................ G01N 03/18
[52] U.S. Cl. ............................ 374/46; 73/827; 228/56.5
[58] Field of Search ............... 374/51, 48, 46; 73/827; 228/196, 56.5

[56] References Cited

U.S. PATENT DOCUMENTS

| | | | |
|---|---|---|---|
| 2,761,310 | 9/1956 | Siegel | 374/48 |
| 3,605,486 | 9/1971 | Anderholm et al. | 73/827 X |
| 3,937,073 | 2/1976 | Steel | 73/842 |
| 4,027,529 | 6/1977 | Olsen | 73/827 |
| 4,393,718 | 7/1983 | Gebhard et al. | 374/49 |
| 4,425,802 | 1/1984 | Sponseller | 73/827 |

FOREIGN PATENT DOCUMENTS

| | | |
|---|---|---|
| 2036770 | 3/1972 | Australia . |
| 0008217 | 2/1980 | European Pat. Off. . |
| 1282812 | 7/1972 | United Kingdom . |

*Primary Examiner*—Daniel M. Yasich
*Attorney, Agent, or Firm*—Gottlieb, Rackman & Reisman

[57] ABSTRACT

The invention provides a non-destructive method of testing a weld made by pressure welding two metal parts (2, 3) at forging temperature. After heating to a temperature of about 1100° C. and applying a forging pressure (F1) to form the weld, the method consists in applying a tensile strength (F2) to the weld perpendicularly to the junction plane (P) between the two ducts (2 and 3) while the weld is still hot at a temperature of, for example, about 600° C., in order to enlarge any defects present at the junction surface (4) and thus make them detectable by a conventional fault detection means.

6 Claims, 2 Drawing Sheets

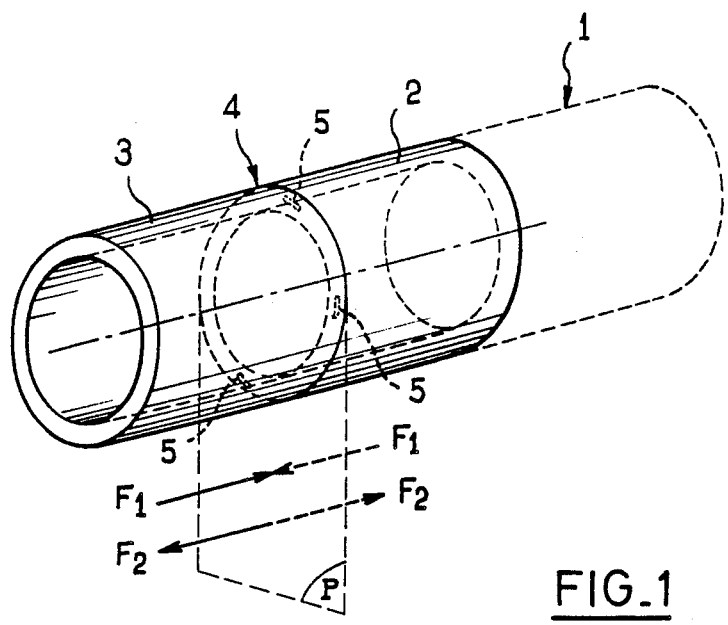
FIG_1
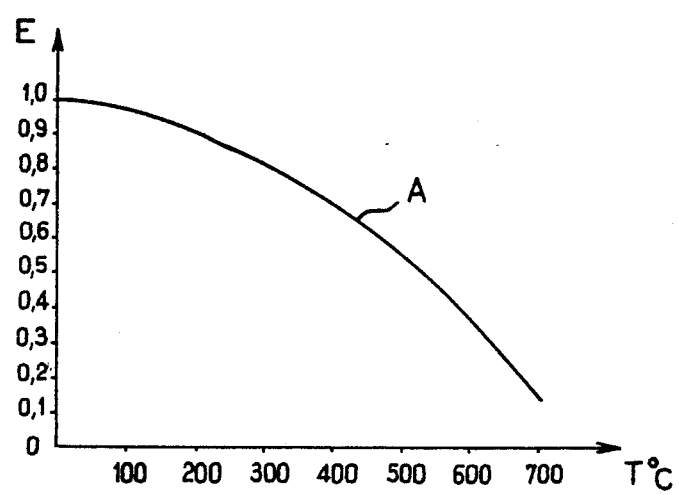
FIG_2

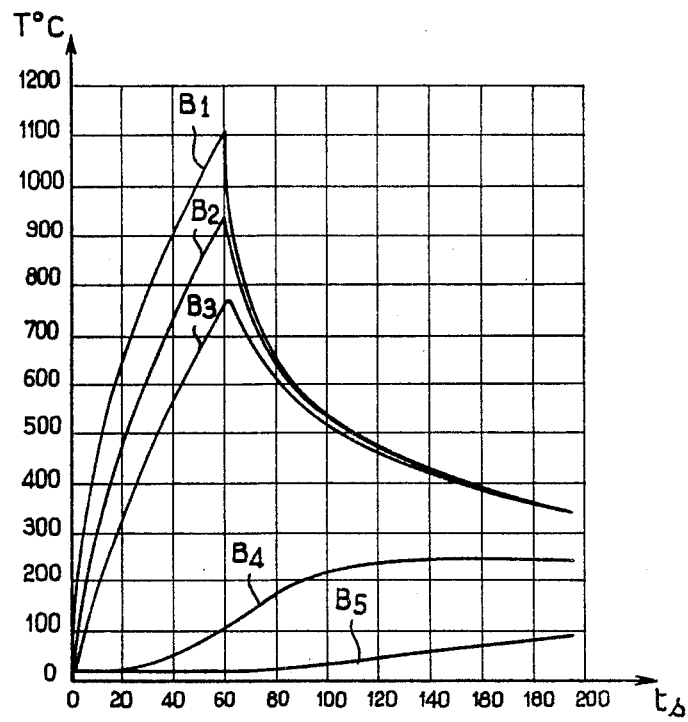
FIG_3
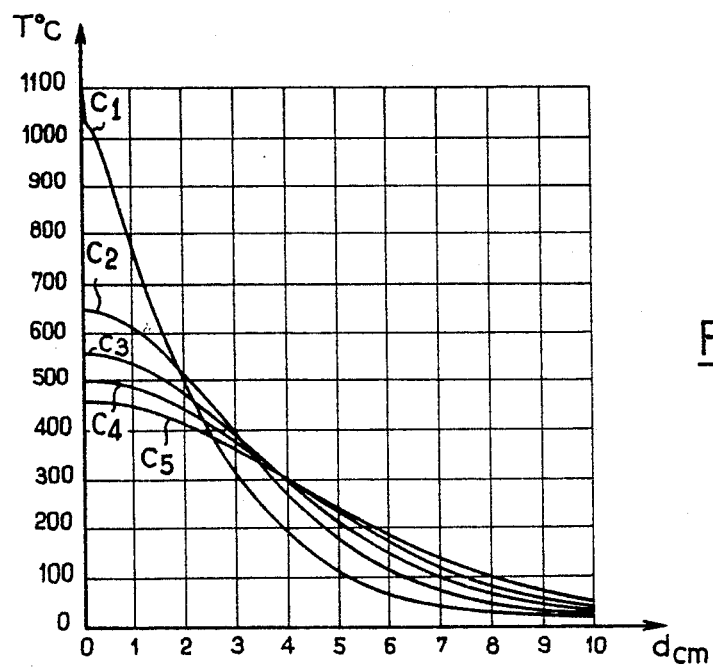
FIG_4

NON-DESTRUCTIVE METHOD OF TESTING A WELD OBTAINED BY PRESSURE WELDING TWO METAL PARTS

The present invention relates to a non-destructive method of testing a weld obtained by pressure welding two metal parts.

BACKGROUND OF THE INVENTION

A method of pressure welding two metal parts, in particular at forging temperature consists in bringing the two parts together and putting them into contact with each other, in heating them up to a certain temperature at their junction surface or join plane, and then in applying a forging pressure, such as a predetermined compression stress, perpendicularly to the join plane during cooling.

Pressure welding methods are known per se, and are widely used in numerous industrial fields, in particular for welding together metal tubes and rails for railway lines, for example. However, the use of such methods in some fields can give rise to problems related to the regulations that must be satisfied. This applies, in particular, to welding high pressure on-shore or off-shore pipelines for transporting oil or gas, where such regulations are extremely severe for obvious safety reasons. In general, all such regulations require a weld to be tested non-destructively after welding in order to detect any faults, and in particular to detect faults in compactness due, for example, to failure to melt in certain points of the weld, to the presence of cracks, to inclusions containing polluting substances such as slag, tungsten, copper, . . . , pockets of gas, etc. Acceptable sizes for each of such defects are specified in great detail in such regulations for determining whether a weld can be accepted or must be rejected, and for each type of fault detected, account is taken of its nature, its extent or volume, and its frequency. For example, such regulations are known by the abbreviations API 1104 in the USA, DNV 1981 for the bed of the North Sea, BS 4515 1984 for Great Britain, and under the name GAZ DE FRANCE for France.

Systems have been developed for testing welds, in particular by means of X-rays, gamma rays, or ultrasound, and these systems provide an image of the weld, which is then analyzed in order to decide whether to accept or reject the weld depending on value specified by the regulations, with the decision optionally also including mechanical tests.

However, although testing systems known in the past work successfully with welds obtained by adding filler material using a moving melt bath, e.g. arc welding, such testing systems are not effective with welds obtained by pressure welding methods. Thus, if steel is heated to a predetermined temperature close to 1100° C. and then has a compression stress applied thereto, any weld defects due to a lack of bonding between the two faces to be welded are highly compressed and become plane. Experience shows that the above-mentioned testing systems based, in particular, on the existence of variations in density are suitable for detecting bulk defects, i.e. defects occupying a certain volume, but are not good at detecting the same defects after they have been compressed.

Preferred implementations of the invention solve the problem of non-destructively testing a weld made by pressure welding, in particular at forging temperature, by causing weld defects to become detectable.

SUMMARY OF THE INVENTION

To this end, the present invention provides a method of non-destructively testing a weld made by hot pressure welding two metal parts, this type of welding consisting in heating said parts at their junction surface to a predetermined temperature and in applying forging pressure such as a predetermined compression stress perpendicularly to said junction surface, the method consisting, after welding, in:

applying a tensile stress perpendicularly to said junction surface and on either side thereof in order to enlarge any defects present at said junction surface, said tensile stress being applied when the junction surface is still hot between a maximum temperature close to the welding temperature and a minimum temperature; and detecting said defects, converted by the tensile stress into bulk or three-dimensional defects, by a conventional fault detector or analyzing system.

The minimum temperature at which the tensile stress is applied should be such that the elastic limit of the metal constituting said parts lies between 30% and 80% of the elastic limit of the metal when cold.

Advantageously, during the welding operation, the contact region or join plane of the parts to be welded is raised to a temperature of about 1100° C., for example, and a tensile stress is applied thereto while the parts are still hot but when the temperature of the join plane has dropped to a temperature lying between 400° C. and 800° C., in particular for metal parts made of steel, for example.

By virtue of these various dispositions, the invention makes it possible to use conventional weld testing or analyzing systems for testing welds made by pressure welding, in particular at forging temperature, thereby enabling such welding methods to be applied to constructing gas and oil pipelines formed by assembling lengths of high pressure ducting together.

BRIEF DESCRIPTION OF THE DRAWINGS

An embodiment of the invention is described by way of example with reference to the accompanying drawings, in which:

FIG. 1 is a diagrammatic perspective view of the method of the invention for welding together two metal ducts;

FIG. 2 is a graph showing variations in the ratio between the elastic limit of a carbon steel at temperature T and the value of the elastic limit of the same steel when cold;

FIG. 3 is a graph having a plurality of curves showing changes in temperature in the join plane of ducts during a welding operation; and FIG. 4 is a graph having a plurality of curves showing temperature distribution at various different instants on either side of the join plane of the ducts.

MORE DETAILED DESCRIPTION

The method of the invention is applied, by way of example, to testing welds in an oil pipeline formed, for example, by connecting together successive tubular metal pieces made of steel, i.e. ducts which are welded end-to-end by a pressure welding method known per se, and more particularly by a method of pressure welding at forging temperature.

With reference to FIG. 1 and in order to outline the testing method in accordance with the invention in an application of the above-mentioned type, the last-welded duct 2 of a pipeline 1 can be seen to which the next duct 3 is connected as described below.

The welding process includes the steps of, during an initial or heating period, positioning duct 3 on the axis of duct 2, putting the two ducts into contact with each other, and heating their junction or contact surface 4 delimiting a join plane P, and thereafter continuing to apply heat until a determined temperature lying between 1100° C. and 1300° C. is reached, i.e. a temperature close to the melting temperature of steel. Heating is performed by conventional methods, e.g.: resistance; induction; electrical discharge; or friction.

Once this heating temperature has been reached, substantially after 60 seconds, the forging operation is performed during a second stage which includes the steps of applying a forging pressure at the junction surface 4 for a period of a few seconds, with the forging pressure being such as to constitute a compression stress of about 10 kg/mm$^2$ perpendicularly to the join plane P as shown by arrows $F_1$–$F_1$ in FIG. 1.

After the forging pressure has been applied, defects 5 that may be present in the welded zone on either side of the junction plane P between the ducts 2 and 3 are compressed and become plane defects. For example, such defects are essentially compactness defects such as zones of incomplete melting, cracking, inclusions of polluting substances such as slag or oxides formed during melting, or pockets of gas, etc. Although such defects are different in nature, they are lumped together in FIG. 1 under the reference 5.

In accordance with the principles of the present invention, after heating and applying the compression stress, the testing method comprises the step of applying a mechanical treatment to the junction surface 4 between the ducts 2 and 3 in order to cause poorly welded zones to come apart so as to transform plane defects 5 into three-dimensional bulk or volume defects.

This mechanical treatment is advantageously a tensile stress applied perpendicularly to the contact surface 4 between the ducts 2 and 3, as indicated by arrows $F_2$–$F_2$ in FIG. 1.

This tensile stress is applied while the contact region is hot for a period of a few seconds at a value close to the elastic limit of the metal, and in particular it is exerted when the temperature of the contact surface 4 between the ducts 2 and 3 has dropped back to a temperature lying between 400° C. and 800° C. for steel, for example.

The tensile stress is exerted while the metal is hot for reasons which are explained with reference to FIGS. 2 to 4.

In FIG. 2, curve A shows how the ratio E between the elastic limit at temperature T and the elastic limit when cold varies with temperature for a carbon steel. Observing curve A shows that the value of the this ratio drops as a function of temperature and that at around 600° C., the elastic limit of the steel is about 30% of its value at 20° C. In other words, the application of the tensile stress at a temperature of about 600° C. has the advantage of limiting the value of the tensile stress to 15 kg/mm$^2$, for example, whereas said value would need to be 45 kg/mm$^2$ at an ambient temperature of 20° C., i.e. at the end of the period during which the contact surface 4 cools down.

In general, the tensile stress is applied while the parts are hot between a maximum temperature corresponding to the welding temperature, i.e. the temperature to which the contact surface 4 is raised before the compression stress is applied, and a minimum temperature such that the elastic limit of the metal is about 80% of the elastic limit of the metal when cold. In other words, the tensile stress is applied while the parts are hot, but at a temperature which varies depending on the steel used.

Since the weld is tested by non-destructive means, it follows that the value of the tensile stress exerted at the contact surface 4 must not exceed a certain or limiting value beyond which there is a danger of breaking the weld between the ducts 2 and 3. It is preferable for the value of the tensile stress applied to lie in the vicinity of the elastic limit of the metal at the temperature of the welded zone, while remaining slightly below said limit, or slightly above said limit, but in any event below the ultimate (breaking) tensile stress value.

In FIG. 3, the various curves B1 to B5 show how the temperature of the junction surface 4 (curve B1) varies as a function of time on either side of the contact surface 4, and respectively at distances of 0.5 cm (curve B2), 1 cm (curve B3), 5 cm (curve B4), and 10 cm (curve B5) from the contact surface.

In FIG. 4, the various curves C1 to C5 show the temperature distribution on either side of the junction surface 4 between the ducts 2 and 3 at various different instants, respectively, with the initial instant corresponding to the end of the operation of heating the junction surface 4. The curves C1 to C5 correspond respectively to elapsed times of 60 seconds (s), 80 s, 95 s, 110 s, and 125 s.

An examination of the curves in FIGS. 3 and 4 shows that for a given tensile stress as a function of the change in temperature at the contact surface 4, i.e. the weld zone (FIG. 3) and as a function of the temperature distribution on either side of the contact surface 4 (FIG. 4), the desired elongation effect is obtained mainly at the contact surface 4, i.e. in the welded zone since it is at the highest temperature.

The application of the tensile stress thus serves to transform plane defects 5 into three-dimensional defects which are entirely detectable by conventional fault detecting or analyzing systems. These systems, for example, may be or includes devices using X-ray or gamma ray radiation, ultrasound, dye penetration, video inspection, etc. These various systems examine the weld and generate an image which is visually inspected in order to determine whether the defects detected satisfy, i.e., are below or above or fail to satisfy the values specified by regulations, depending on the sizes of the defects, in order to decide whether the weld can be accepted or rejected.

The means required for implementing the method of the invention are available to the person skilled in the art. For example, one way of applying tensile stress to the welded joint while the same is still hot after the forging operation (compression stress) is to use a single actuator providing controlled force and/or controlled displacement. However, in pressure welding methods, it is conventional to make use of a plurality of force applying devices for applying the compression stress during the forging operation. Thus, by using the double-acting force applicators, the same can advantageously be used for applying the both the compressive stress for forming the weld as well as the tensile stress for testing the weld for faults or defects in accordance with the invention. The control signal for applying the tensile stress may advantageously include a servo-control loop relating the parameters: tensile stress value; metal elongation; time during which the stress is applied; and temperature at which said stress is applied; in order to take account, in particular, of the nature of the steel used to make the ducts 2 and 3.

The testing method of the invention finds particular utility in the construction of oil and gas pipelines, and more generally in the inspection of welds of high pressure ducting, and it opens up highly advantageously perspectives, in particular concerning the means required for its implementation which do not add to the heavy and expensive means already required for such construction.

Naturally, the invention is not limited to the above-described example, but includes any variant based on the principle which consists in using tensile stress to enlarge weld defects following a forging operation in pressure welding during which the defects were formed. Further, although the method of the invention is applied more particularly to a method of pressure welding at forging temperature, the invention is applicable more generally to any method of pressure welding two metal parts, with or without a space being provided between the parts, with or without prior docking pressure, and with an arbitrary junction surface between the two parts.

I claim:

1. In a method of non-destructively testing a weld between two metal parts butt-welded to each other at their junction surface by being heated to a predetermined welding temperature and subjected to a forging pressure applied to said parts so as to exert thereon a predetermined compression stress directed perpendicularly to said junction surface and of such a magnitude as to compact any defects in the weld to a substantially plane state; the improvement comprising the steps of:

applying a tensile stress to said weld perpendicularly to said junction surface of said parts and on either side thereof directly after completion of the welding operation and while the weld is still hot between a maximum temperature close to the welding temperature and a predetermined minimum temperature, thereby to enlarge any defects in the weld present at said junction surface into a three-dimensional state; and inspecting said weld with the aid of conventional fault detection means for detecting said three-dimensional defects.

2. A testing method according to claim 1, wherein said tensile stress is applied to said weld at a temperature at which the elastic limit of the metal constituting said parts in the weld zone lies between 30% and 80% of the elastic limit of that metal when cold.

3. A testing method according to claim 1, wherein the magnitude of said tensile stress applied to said weld is close to the elastic limit of the metal in the weld zone where the temperature is highest.

4. A testing method according to claim 1, wherein the magnitude of said tensile stress applied to said weld is such that the elastic the limit of the metal is exceeded, at least locally, in the weld zone where the temperature is highest.

5. A testing method according to claim 1, wherein the temperature of said parts at said junction surface during said heating operation is about 1100° C., and said tensile stress is applied to said weld while the same is still hot at a temperature at the junction surface of between about 400° C. and 800° C.

6. A testing method according to claim 5, wherein the metal parts are made of steel.

* * * * *